United States Patent [19]

Mitsuyasu et al.

[11] Patent Number: 5,247,136

[45] Date of Patent: Sep. 21, 1993

[54] RESIN CORED ENCLOSED FINE METAL WIRES AND APPARATUS FOR MANUFACTURE THEREFORE

[75] Inventors: Kazuyuki Mitsuyasu; Tatsuji Hirano, both of Toyota, Japan

[73] Assignee: Fuji Polymer Industries Co., Ltd., Aichi, Japan

[21] Appl. No.: 749,947

[22] Filed: Aug. 26, 1991

[30] Foreign Application Priority Data

Aug. 27, 1990 [JP] Japan ................................. 2-225548

[51] Int. Cl.$^5$ ................................................ H01B 7/00
[52] U.S. Cl. ............................ 174/113 R; 174/110 S; 174/113 AS
[58] Field of Search ........ 174/113 R, 113 AS, 113 A, 174/114 R, 114 S, 110 S; 128/419 P, 784, 785, 786

[56] References Cited

U.S. PATENT DOCUMENTS

| | | | |
|---|---|---|---|
| Re. 24,154 | 5/1956 | Krueger | 174/113 AS |
| 2,804,494 | 8/1957 | Fenton | 174/113 AS |
| 3,680,544 | 8/1972 | Shinnick et al. | 128/419 P X |
| 4,484,586 | 11/1984 | McMickle et al. | 128/786 |
| 4,734,545 | 3/1988 | Susuki et al. | 174/113 A |
| 4,920,980 | 5/1990 | Jackowski | 128/786 |
| 4,945,342 | 7/1990 | Steinemann | 174/113 R |
| 5,092,333 | 3/1992 | Tsuchida et al. | 128/786 |

FOREIGN PATENT DOCUMENTS 749966  6/1956  United Kingdom ......... 174/113 AS

OTHER PUBLICATIONS

"Handbook of Silicone Rubber Fabrication", Wilfred Lynch, 1978, pp. 97-133; Van Nostrand Reinhold Company.

*Primary Examiner*—Morris H. Nimmo
*Attorney, Agent, or Firm*—Fish & Richardson

[57] ABSTRACT

An apparatus for manufacturing a resin cord with enclosed fine metal wires is provided as a unit, in which fine metal wires are supplied from a nipple to a die while extruding a resin around the nipple into the die for burying the fine metal wires in the resin in the length direction of a hollow or solid resin cord, the nipple having a central space in its section perpendicular to the extruding direction and also fine metal wire supply grooves joining the central space, a nozzle made of a wear-resistant material being provided in the central space. The outer diameter of the cord is 0.3 to 2.0 mm, the thickness of the resin part is 0.1 mm or above, the diameter of fine metal wires is 0.03 to 0.2 mm, and the thickness of the resin part is greater than the diameter of the fine metal wires.

3 Claims, 3 Drawing Sheets

RESIN CORED ENCLOSED FINE METAL WIRES AND APPARATUS FOR MANUFACTURE THEREFORE

FIELD OF THE PRESENT INVENTION

This invention relates to resin cords with enclosed fine metal wires, which are useful as medical catheters, tubes enclosing electric wires and small diameter electric wires, and also to a method of manufacturing such cords.

BACKGROUND OF THE INVENTION

Heretofore, the extrusion process for manufacturing resin-covered electric wires or the like has usually been performed by the cross head method. This prior art technique will now be described with reference to the drawings.

FIG. 7 is a sectional view showing a prior art cross-head apparatus. Referring to FIG. 7, designated at 12 is an extruder or the like for extruding resin 13, at 15 a die for molding the resin into a predetermined shape, at 14 a nipple for guiding the resin, at 16 a mandrel for leading a supplied wire, at 17 an adjustment nut, and at 18 a keyway (or a main fluid path).

The operation of the above prior art apparatus will now be described.

Resin extruded from the extruder 12 is forced out through the keyway 18, around the nipple 14 and through the die 15. Meanwhile, a wire 2 is supplied from a wire inlet and passes through the center of the nipple inside into the die 15. The resin 13 is molded around the wire 2 to produce a wire 1 which is covered with resin. The covered wire 1 is rolled up outside the die 15. When silicone rubber is used, the covered wire emerging from the die 1 is vulcanized in a tunnel oven or furnace (not shown) or the like before being rolled up.

The prior art nipple 14 for manufacturing electric wires is merely a hollow one through which wires can be passed. For manufacturing a catheter, a nipple as shown in FIGS. 8 and 9 is used.

Referring to FIGS. 8 and 9, the nipple 14 has diametrically opposed small bores 19 for supplying electric wires 2 therethrough and a central small bore 20. Through the central small bore 20, air or like gas is supplied under slight pressure into the central portion of the catheter to prevent squeezing of the central portion.

Heretofore, wire-enclosed cords such as wire-enclosed tubes, medical catheters and small diameter electric wires have not been in high demand so that those cords have not been required to be very fine, and thus they can be sufficiently formed with the nipple as shown in FIGS. 8 and 9. However, recently developed very fine wire-enclosed cords such as wire-enclosed tubes, medical catheters and small diameter electric wires cannot be manufactured using the prior art nipple. This is problematic for the following reasons.

(1) Thin metal wires can protrude out of the resin portion of the cord.

(2) The provision of an independent bore for supplying a thin metal wire therethrough requires sophisticated and difficult processing.

(3) In the prior art, it is possible to process a bore to a depth (or length) of about 3 to 5 times as large as the fore diameter the bore diameter. This means that a tip portion of the mandrel is deformed due to the resin extruding force.

(4) Wear due to passage of fine metal wire is significant, and early replacement of the nipple is necessary.

For the above reasons, very fine wire-enclosed cords such as wire-enclosed tubes, medical catheters and electric wires could have not been obtained by the prior art method.

SUMMARY OF THE INVENTION

In order to solve the above problems inherent in the prior art, it is an object of the invention to provide a very fine wire-enclosed resin cord which could not have heretofore been obtained and also a method of manufacturing the same.

To attain the above object of the invention, there is provided a resin cord with enclosed fine metal wires extending in the longitudinal direction of a hollow or solid resin part, the outer diameter of the resin cord ranging from 0.3 to 2.0 mm, the thickness of the resin part being 0.1 mm or larger, the diameter of the fine metal wires ranging from 0.03 to 0.2 mm, the thickness of the resin part being larger than the fine metal wire diameter.

In this structure, the resin is preferably silicone rubber and the fine metal wires are silver, copper or stainless steel wires.

Further in this structure, preferably two or more fine metal wires are buried independently within the resin of the cord.

According to the invention there is also provided an apparatus for manufacturing a resin cord with enclosed fine metal wires comprising a unit, in which fine metal wires are supplied from a nipple to a die while extruding resin around the nipple into the die to imbed the fine metal wires in the resin in the lengthwise direction of a hollow or solid resin cord, the nipple having a central space extruding perpendicular to the extruding direction and also fine metal wire supply grooves joining the central space, a nozzle made of a wear-resistant material being provided in the central space.

In this structure of the apparatus, preferably the nozzle is made of a material selected from a group consisting of sapphire and ceramics.

Further, in the apparatus structure preferably the length of the fine metal wire supply grooves is over 10 times the diameter of fine metal wires passed through the grooves.

DETAILED DESCRIPTION OF THE INVENTION

In the structure according to the invention, the outer diameter of the cord is 0.3 to 2.0 mm, the thickness of the resin part is 0.1 mm or larger, the diameter of fine metal wires is 0.03 to 0.2 mm, and the thickness of the resin part is greater than the diameter of the fine metal wires. Thus, very fine metal wires of high quality can be made. More specifically, it is possible to obtain a resin cord with enclosed fine metal wires, in which fine metal wires are accurately buried in the resin without protruding out of the resin's surface in spite of the thin character of the resin part.

In addition, in a preferred structure according to the invention the resin is silicone rubber and the fine metal wires are silver, copper or stainless steel wires, such desired properties as flexibility, sanitation and freedom from adverse effects on the human body can be provided to medical catheters and the like.

In a further preferred structure according to the invention two or more fine metal wires are buried independently, so it is possible to supply power to an operating object at the distal end of a tube with enclosed electric wires or catheters.

Further, with the structure of the apparatus according to the invention, in which the nipple has a central space in its section perpendicular to the extruding direction and also fine metal wire supply grooves joining the central space, precision processing can be performed without need of providing any independent fine metal wire supply bore. Further, with the nozzle of a wear-resistant material provided in the central space of the nipple, the extruding process can be performed stably over a long period of time without wear of the nozzle even where fine metal wires are supplied continuously through the grooves. Thus, a resin cord with enclosed fine metal wires can be manufactured efficiently and logically.

In another further preferred structure of the apparatus according to the invention the nozzle is made of a material selected from the group consisting of sapphire and ceramics, making it is possible to further improve the wear resistance of the nozzle.

In yet another preferred structure of the apparatus according to the invention the length of the fine metal wire supply grooves is over 10 times the diameter of the fine metal wires which pass through the grooves. So stable manufacture is possible without deformation of the nipple even with considerably increased pressure applied to the resin being extruded for molding.

Now, embodiments of the invention will be described with reference to the drawings.

Figure 2:
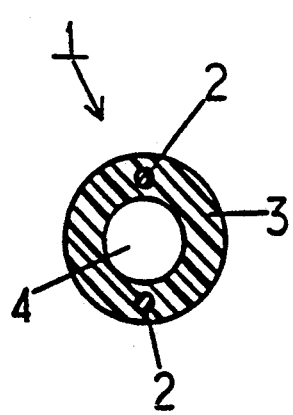
FIG. 2 is a transversal sectional view of the resin cord of FIG. 1.
Figure 1:
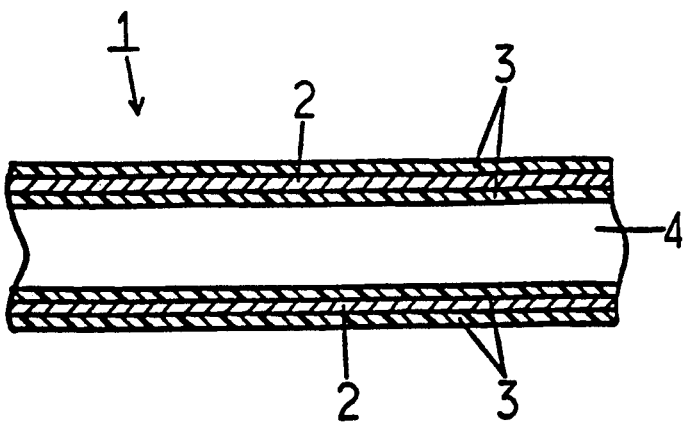
FIG. 1 is a longitudinal sectional view showing an embodiment of the resin cord with enclosed fine metal wires according to the invention.

FIGS. 1 and 2 show an embodiment of the resin cord with enclosed fine metal wires according to the invention. Referring to FIGS. 1 and 2, designated at 1 is a tube with enclosed electric wires, at 2 are fine metal wires, at 3 a resin part, and at 4 a space portion.

In the tube 1 with enclosed electric wires having the above construction, fine metal wires 2 are buried substantially in a central portion of the wall of the resin part 3 such that they extend longitudinally. The tube 1 with enclosed electric wires has an outer diameter of 0.3 to 2.0 mm, preferably 0.85 to 1.5 mm. If the outer diameter is less than 0.3 mm, it is difficult to insert the fine metal wires. If the outer diameter is greater than 2.0 mm, it is too large and impractical.

The resin part has a thickness of 0.1 mm or larger or bigger. This is so in order to cover the fine metal wires.

It is further necessary that the diameter of the fine metal wires ranges from 0.03 to 0.2 mm and that the the thickness of the resin part is greater than the diameter of the fine metal wires. This is so in order to completely bury very fine metal wires in the resin part. Preferably, the diameter of the fine metal wires ranges from 0.05 to 0.15 mm, the inner diameter of the tube (i.e., diameter of the space 4) ranges from 0.3 to 0.5 mm, and the thickness of the resin part 3 ranges from 0.1 to 0.5 mm.

The material of the resin part 3 may be any resin, but silicone rubber is preferred in view of its flexibility, sanitary properties and suitability for use in the human body.

The fine metal wires 2 may be made of copper in the case of the electric wire. In the case of the catheter, however, it is preferably made of silver or stainless steel.

Further, in view of securing the power source, preferably two or more fine metal wires are buried independently. As an example, 2 to 10 wires can be buried independently.

It is possible that a metal wire or metal wires may be inserted through the space 4. Further, the space 4 may be replaced with solid resin in cases other than catheters, for instance small diameter electric wires.

Figure 3:
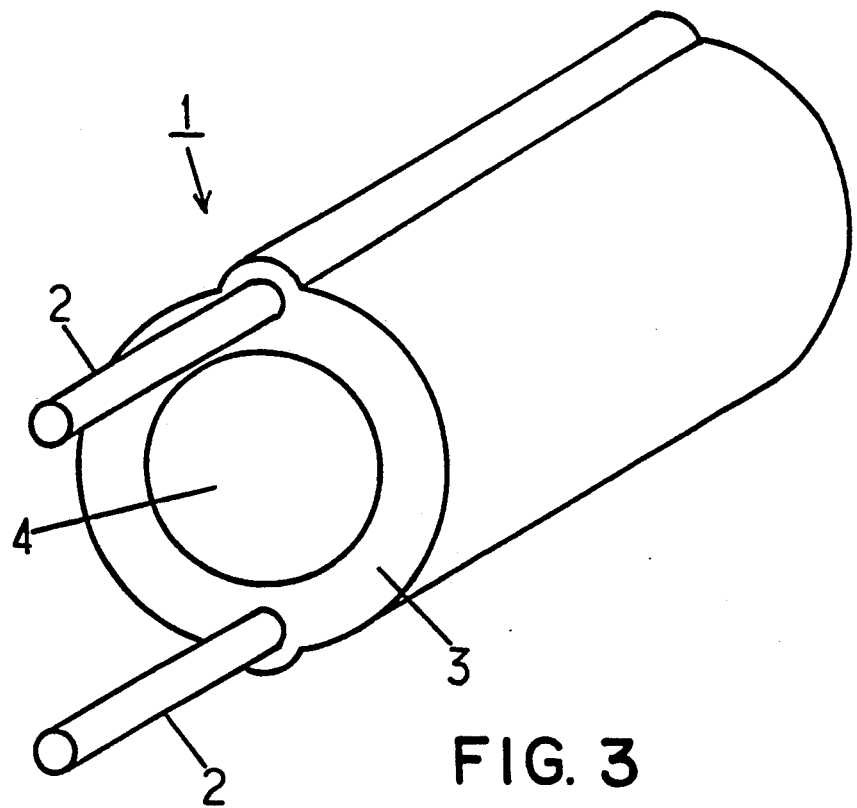
FIG. 3 is an oblique partially cut-away view showing a different embodiment of the resin cord with enclosed fine metal wires according to the invention.

FIG. 3 shows a tube with enclosed electric wires as a different embodiment of the invention. This embodiment is different from the embodiment shown in FIGS. 1 and 2 in that raised portions are provided to enclose fine metal wires 2.

Figure 4:
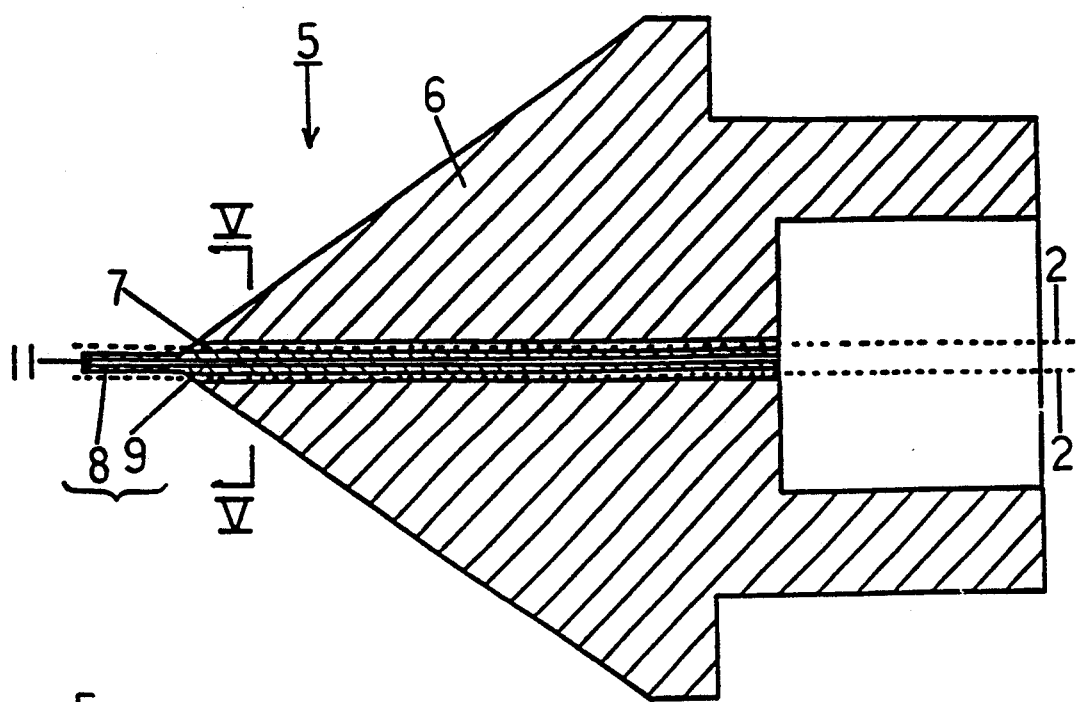
FIG. 4 is a sectional view showing a nipple embodying the invention.
Figure 5:
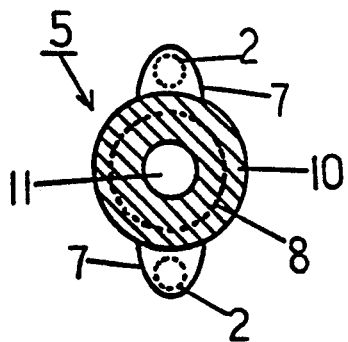
FIG. 5 is a sectional view taken along line V—V in FIG. 4.

FIGS. 4 and 5 show a nipple structure as an embodiment of the invention. Referring to FIGS. 4 and 5, designated at 5 is a nipple, and at 6 a resin guide. Resin is forced out around the guide 6 and nozzle tip section 6 toward a die (not shown). Designated at 7 are grooves for supplying fine metal wires 2 therethrough. The grooves 7 formed are to join the space for inserting nozzle section 10 therethrough. Designated at 8 is a nozzle tip section for forming the inner space of the resin tube, at 9 is a nozzle insert section to be inserted in the nipple 5, at 10 is a nozzle section, and at 11 is a central small bore for slight pressure application to form the resin tube inner space.

The function of the nipple 5 having the above construction will now be described.

Figure 6:
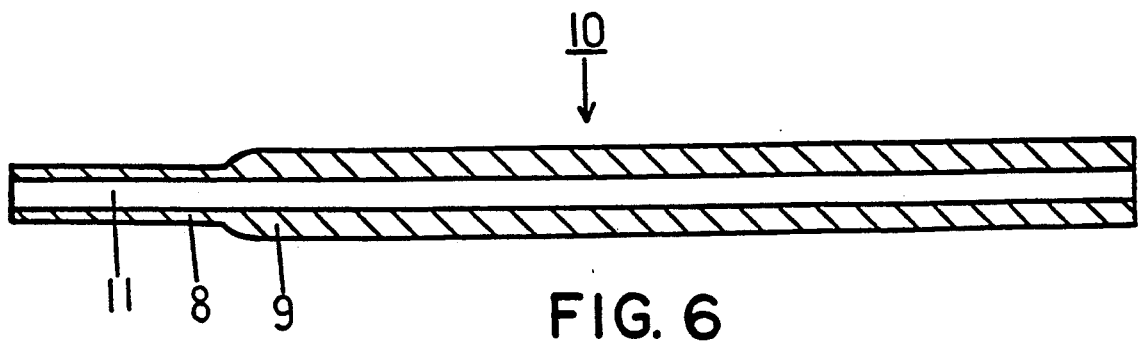
FIG. 6 is a sectional view showing a nozzle 10.
Figure 7:
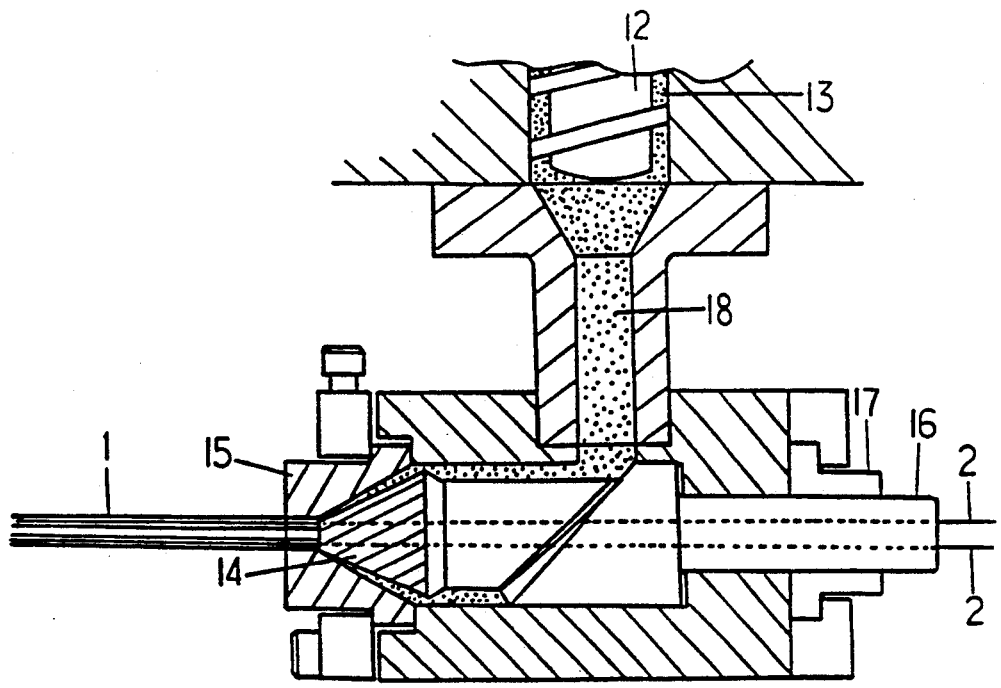
FIG. 7 is a sectional view showing a prior art cross-head apparatus.
Figure 9:
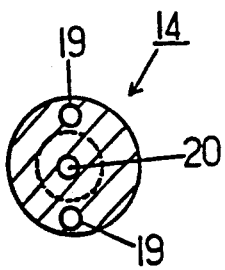
FIG. 9 is a sectional view taken along line IX—IX in FIG. 8.
Figure 8:
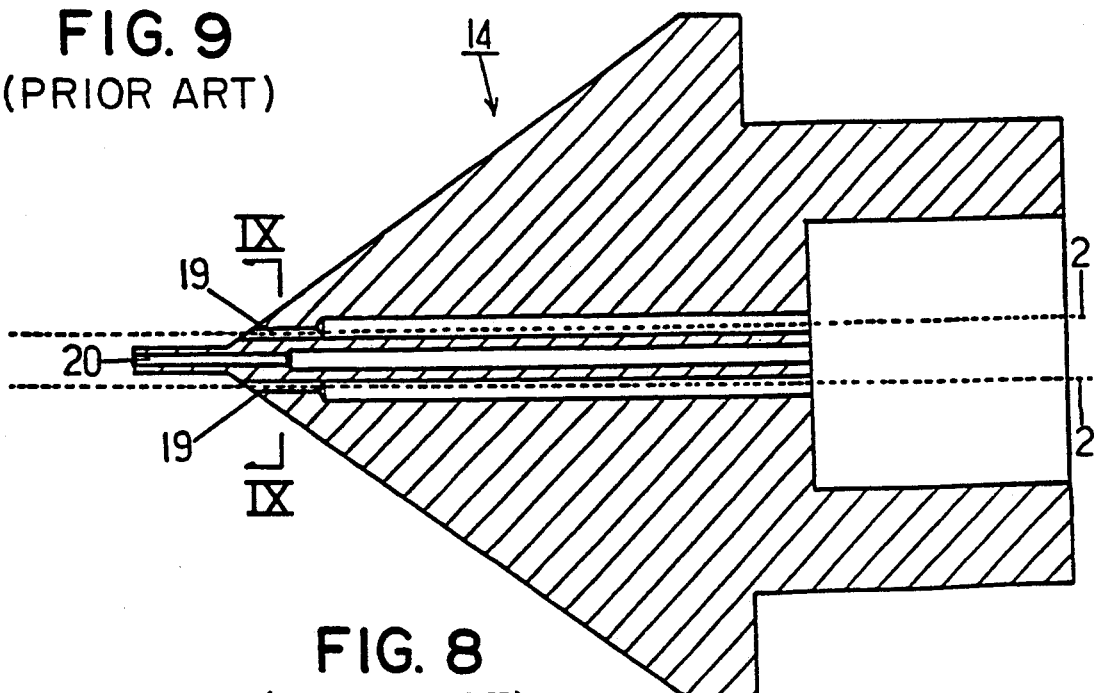
FIG. 8 is a sectional view showing a prior art nipple.

Nozzle section 10 shown in FIG. 6 and made of sapphire was inserted into the nipple 5, which was in turn installed in an apparatus which was basically the same as the apparatus shown in FIG. 7. As for the dimensions of the grooves 7 of the nipple 5, the diameter was 0.15 nm (or 150 micrometers), and the depth was 19 mm. Stainless steel wires (SUS316) with a diameter of 0.1 mm (or 100 micrometers) were supplied to the grooves 7. When dealing with fine stainless steel wires, it is convenient to first remove the nozzle section 10, then insert the stainless steel wires into the grooves 7 and then insert the nozzle section 10.

The nozzle tip section 8 of the nozzle 10 had a diameter of 0.50 mm, the nozzle insert section had a diameter of 0.65 mm, the central small bore had a diameter of 0.20 mm, and the overall length was 19 mm. Silicone rubber was extruded at room temperature and at an extruding speed of 20 m/min. During this time, the die was water-cooled. The eventual product emerging from the die was passed through a tunnel oven or furnance having a length of 6 m and holding at a temperature of 250° C. to vulcanize it.

The tube with enclosed electric wires thus obtained had an average outer diameter of 0.8 mm, space diameter of 0.4 mm and a resin part thickness of 0.2 mm. All the fine metal wires were found substantially contained in the central portion of the resin part. The apparatus was operated continuously for one week, and no wear of the nipple or mandrel was observed.

The above embodiment has the following advantages.

(1) It is possible to obtain a very fine resin cord with enclosed fine metal wires which could have never been obtained. Such fine resin cord with enclosed fine metal wires is very useful as tubes with enclosed electric wires, medical catheter and small electric wires.

(2) Fine metal wires can be located stably is substantially the central portion of the resin part.

(3) The fine nipple bores for supplying fine metal wires therethrough can be provided accurately.

(4) It is possible to provide a bore depth or length which is over ten times the bore diameter and sufficiently withstand the resin extrusion pressure.

(5) There is no problem in the wear resistance even in the case of fine metal wires.

(6) Since the nozzle section is removable, it is possible to readily supply fine metal wires by first removing the nozzle section, then passing the fine metal wires through the nipple and then inserting the nozzle section into the nipple.

As has been described in the foregoing, according to the invention a resin cord with very fine metal wires buried in the resin can be obtained accurately and without possibility of the metal wires protruding from the resin.

It is a further preferred structure according to the invention that two or more fine metal wires are buried independently. With this structure, it is possible to supply electric power to a distal operating part of a tube with enclosed electric wires or a catheter.

Further, with the apparatus according to the invention the nipple has a central space in a section perpendicular to the extruding direction and also fine metal wire supply grooves joining the central space. Therefore, precision processing can be readily performed without the need of providing independent fine metal wire supply bores. Further, since the central space of the nipple is provided with a nozzle made of a wear-resistant material, the extrusion processing can be performed stably over a long time and without wear of the nozzle even in the case where fine metal wires are supplyied continuously through the grooves. Thus, a resin cord with very fine metal wires enclosed therein can be obtained efficiently and logically.

A further preferred structure of the apparatus according to the invention is that the nozzle is made of sapphire or ceramics. In this case, wear-resistant property of the nozzle can be further improved.

A still further preferred structure of the apparatus according to the invention is that the length of the fine metal wire supply grooves is over 10 times the diameter of the fine metal wires inserted into the grooves. In this case, stable manufacture without deformation of the nipple is possible even with considerably increased pressure on the resin being extrusion molded.

We claim:

1. A resin cord comprising fine metal wires enclosed entirely within a hollow or solid resin part extending substantially in a straight line and in the longitudinal direction of said resin part, the outer diameter of said resin cord ranging from 0.3 to 2.0 mm, the thickness of said resin part being 0.1 mm or above, the diameter of said fine metal wires ranging from 0.03 to 0.2 mm, said resin part thickness being greater than said fine metal wire diameter.

2. A resin cord with enclosed fine metal wires according to claim 1, wherein said resin part is made of silicone rubber, and said fine metal wires are made of a member selected from the group consisting of silver, copper and stainless steel.

3. The resin cord according to claim 1, wherein two or more fine metal wires are substantially parallel to one another and each fine metal wire is enclosed independently within the resin cord.

* * * * *